United States Patent [19]

Brinker

[11] Patent Number: 5,131,633
[45] Date of Patent: Jul. 21, 1992

[54] APPARATUS FOR RETRIEVING A SLAG SAMPLE DURING A STEELMAKING OPERATION

[75] Inventor: Dale W. Brinker, Allentown, Pa.

[73] Assignee: Bethlehem Steel Corporation, Bethlehem, Pa.

[21] Appl. No.: 783,649

[22] Filed: Oct. 28, 1991

Related U.S. Application Data

[63] Continuation of Ser. No. 571,476, Aug. 23, 1990, abandoned.

[51] Int. Cl.$^5$ .............................................. C21B 7/24
[52] U.S. Cl. .................................. 266/79; 73/DIG. 9
[58] Field of Search .......................... 266/79, 204, 225; 73/423, DIG. 9

[56] References Cited

U.S. PATENT DOCUMENTS 3,753,372  8/1973  Collins ............................ 73/DIG. 9

*Primary Examiner*—Scott Kastler
*Attorney, Agent, or Firm*—John I. Iverson; Harold I. Masteller, Jr.

[57] ABSTRACT

Apparatus for retrieving a sample of slag from the surface of molten steel contained in a ladle. A hoist positioned above the ladle lowers and raises an elongated metal rod which has cardboard and metal sleeves surrounding the lower portion of the elongated metal rod. A clean sample of molten slag tightly adheres to the metal sleeve as it is raised from the molten slag layer. The metal sleeve and slag sample are easily removed from the elongated metal rod for analysis.

5 Claims, 2 Drawing Sheets

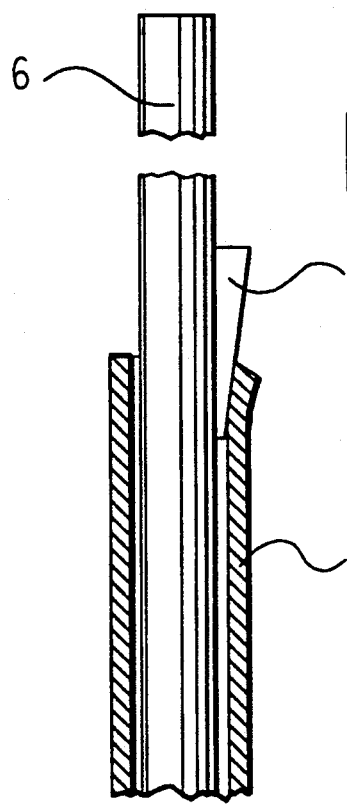
Fig. 2
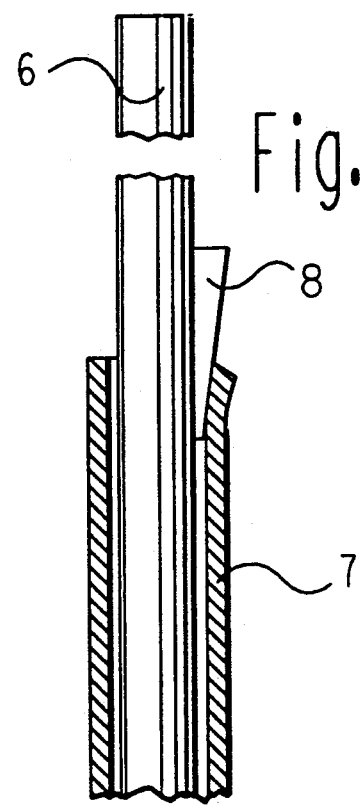
Fig. 3
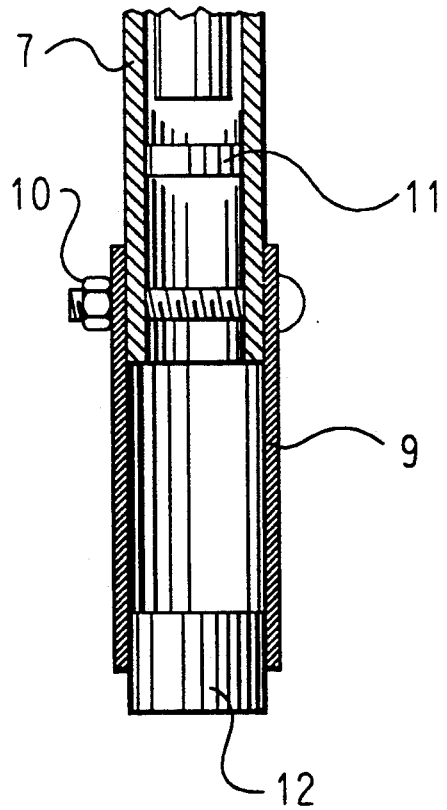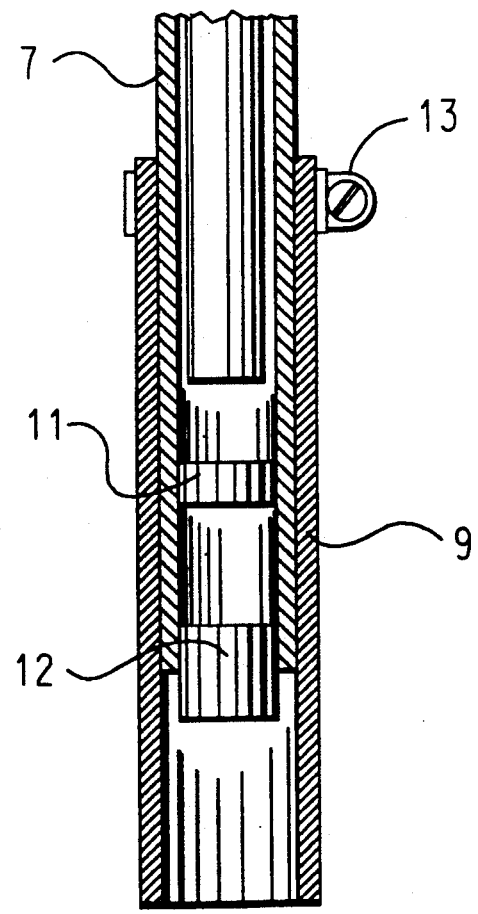

APPARATUS FOR RETRIEVING A SLAG SAMPLE DURING A STEELMAKING OPERATION

This is a continuation of co-pending application Ser. No. 07/571,476 filed on Aug. 23, 1990, now abandoned.

BACKGROUND OF THE INVENTION

This invention relates to apparatus for use in steelmaking. It relates particularly to apparatus used to obtain a representative sample of molten slag floating on the surface of molten steel contained in a ladle or similar vessel.

Molten steel after it is refined in a steelmaking furnace, such as a basic oxygen furnace, is tapped into a refractory lined ladle where it is refined further at a ladle treatment station and then transferred to a continuous casting machine or poured into ingots. Modern high quality steels are usually further refined and treated at a ladle treatment station to remove impurities such as sulfur by injecting lime, calcium-silicon or magnesium to the steel or adding various other refining or alloying materials. The injection of these refining or alloying materials into the steel is usually done by a submerged lance at the ladle treatment station. The injection of these materials into the steel produces a slag on the surface of the steel.

Analysis of the slag produced on the steel in the ladle is an effective way to monitor the ladle treatment process for the steel. Prior to this invention, steelmakers attempted to obtain samples of the slag for analysis by manually inserting a pipe into the steel in the ladle. Not only is such a practice hot and dangerous, the design of ladle treatment stations frequently prevents access to the ladle for manual slag sampling. Furthermore, the manual sampling often failed to retrieve a representative sample of the slag.

SUMMARY OF THE INVENTION

It is an object of this invention to provide apparatus for obtaining a sample of slag from the surface of molten steel contained in a ladle.

It is a further object of this invention to provide apparatus for obtaining a sample of slag that is safe and reliable.

It is a still further object of this invention to provide apparatus for obtaining a sample of slag that is easily adapted to a ladle treatment process and station.

BRIEF DESCRIPTION OF THE DRAWINGS

FIG. 2 is a sectional view of one embodiment of the slag sampler of this invention.

FIG. 3 is a sectional view of a second embodiment of the slag sampler of this invention.

DESCRIPTION OF A PREFERRED EMBODIMENT

Figure 1:
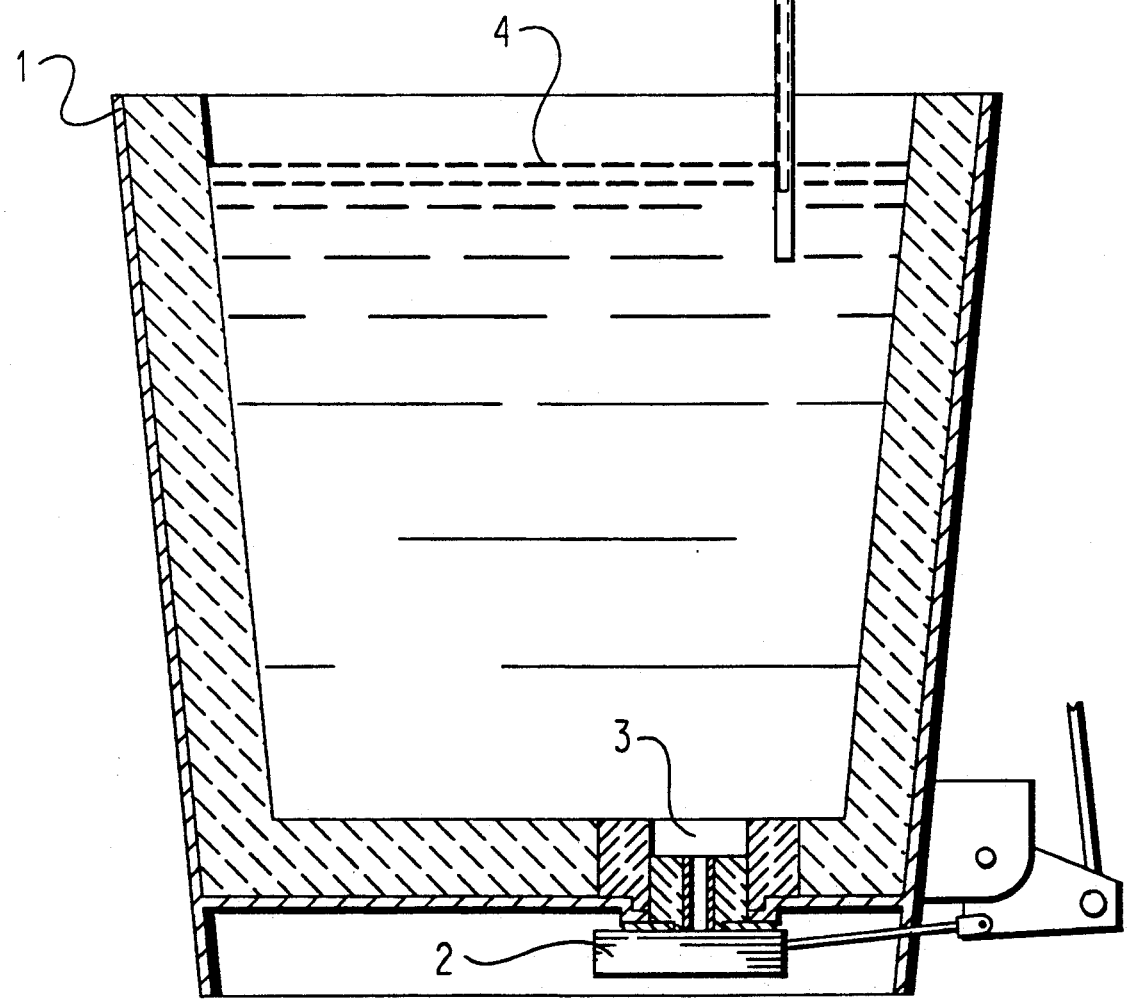
FIG. 1 is a sectional view of a steel transfer ladle illustrating the apparatus used in this invention.

FIG. 1 illustrates a preferred embodiment of the apparatus of this invention. Ladle 1 is a conventional refractory lined ladle used by steelmakers to move molten steel by crane to various locations. Ladle 1 is equipped with a slide gate valve 2 under the ladle nozzle 3 to control the discharge of molten steel from the ladle 1.

A layer of molten slag 4 floats on the surface of the steel. The slag is in part carried over from the steel refining furnace and is in part produced by the introduction of steel refining materials such as lime, calcium-silicon or magnesium. Such materials are added to the ladle by a submerged lance (not shown) as needed.

As shown in FIG. 1, a hoist mechanism 5 is positioned above the ladle 1 which supports an elongated solid metal rod 6. The hoist mechanism 5 is capable of raising or lowering the rod 6 relative to the surface of the molten slag 4 in the ladle 1. Rod 6 can be solid or hollow.

As shown in FIG. 2, the lower end of rod 6 is fitted with a cardboard sleeve 7 which is secured to the rod 6 by a locking wedge 8 which engages the upper end of the cardboard sleeve 7. A tubular metal sleeve 9 is attached to the bottom of the cardboard sleeve 7 by a nut and bolt 10. If desired, a solid cylindrical metal baffle 11 is placed just below the bottom of rod 6 is rod 6 is hollow. If rod 6 is solid, the baffle 11 would not be required. Baffle 11 prevents the entry of any flame or molten steel into the center of rod 6, if it is hollow.

The outside surface of the tubular metal sleeve 9 is preferably roughened and is closed at its lower end by a plug 12 welded into place.

FIG. 3 illustrates another embodiment of the apparatus of this invention in which the cardboard sleeve and the metal sleeve are joined by a circular clamp 13. In this embodiment, the end of rod 6 extends a considerable distance inside metal sleeve 9. The large mass of metal in the lower end of rod 6 acts as a heat sink and will cause the molten slag to solidify faster on the outer surface of metal sleeve 9 then the embodiment shown in FIG. 2.

In operation, the cardboard sleeve 7 is slid onto the end of rod 6 and held in place with a locking wedge 8. The hoist mechanism 5 then lowers the rod 6 down sufficiently so that the metal sleeve 9 is immersed in the molten slag. The hoist is then reversed to raise the rod 6 and sleeve 9 up and away from the ladle 1. The sleeve 7 is then knocked free of wedge 8 and the slag sample which adheres to the outside of the sleeve 9 is retrieved for analysis.

A specific example used a solid 2" diameter rod 6 fitted with a 2¼" diameter cardboard sleeve 36" long connected to metal sleeve 9 of 2¼" diameter and 48" long. The sample apparatus was successful in retaining a slag sample 2 mm thick.

I claim:

1. Apparatus for retrieving a sample of slag from the surface of molten metal in a ladle, comprising:

a) an elongated metal rod having a first end inserted within one end portion of a cardboard sleeve and frictionally attached thereto, b) a tubular metal sleeve including a first end portion adapted to receive a second end of said cardboard sleeve, and a second end portion adapted to receive a plug, said tubular metal sleeve further including an inside surface and an outside surface, said outside surface being additionally roughened to cause a sample of said slag to adhere tightly thereto, c) an interior chamber extending between said plug, inserted into said second end portion of said tubular metal sleeve, and said first end of said elongated metal rod, and d) a baffle located within said interior chamber, said baffle positioned between said plug and said first end of said elongated rod, whereby said plug prevents molten metal or slag from entering said interior chamber, and said baffle further prevents said molten metal or slag from entering said interior chamber.

2. The apparatus of claim 1 wherein said additionally roughened outside surface is capable of adhering to at least a 2 mm thick sample of said molten slag.

3. The invention recited in claim 1 wherein a heat sink is provided within said interior chamber portion, said heat sink adjacent said inside surface of said tubular metal sleeve.

4. The invention recited in claim 1 wherein said cardboard sleeve is frictionally attached to said elongated metal rod by a wedge.

5. The invention recited in claim 1 wherein said plug is inserted into a second end of said cardboard sleeve.

* * * * *